(12) United States Patent
Nevo

(10) Patent No.: US 10,111,419 B2
(45) Date of Patent: Oct. 30, 2018

(54) MULTI-MODAL BIOPSY STORAGE DEVICE AND METHODS

(71) Applicant: Erez Nevo, Netanya (IL)

(72) Inventor: Erez Nevo, Netanya (IL)

( * ) Notice: Subject to any disclaimer, the term of this patent is extended or adjusted under 35 U.S.C. 154(b) by 242 days.

(21) Appl. No.: 14/941,918

(22) Filed: Nov. 16, 2015

(65) Prior Publication Data

US 2016/0135448 A1    May 19, 2016

Related U.S. Application Data

(60) Provisional application No. 62/123,388, filed on Nov. 17, 2014.

(51) Int. Cl.
| | | |
|---|---|---|
| *A01N 1/00* | (2006.01) | |
| *A01N 1/02* | (2006.01) | |
| *A61B 10/00* | (2006.01) | |
| *G01N 1/04* | (2006.01) | |
| *G01N 1/36* | (2006.01) | |
| *G01N 1/31* | (2006.01) | |

(52) U.S. Cl.
CPC ......... *A01N 1/0257* (2013.01); *A01N 1/0252* (2013.01); *A61B 10/0096* (2013.01); *G01N 1/04* (2013.01); *G01N 1/36* (2013.01); *G01N 2001/315* (2013.01); *G01N 2001/366* (2013.01)

(58) Field of Classification Search
CPC ....................................................... G01N 1/00
See application file for complete search history.

(56) References Cited

U.S. PATENT DOCUMENTS

| | | | |
|---|---|---|---|
| 7,560,689 B2 * | 7/2009 | Ban ...................... | H01J 49/0418 250/281 |
| 2007/0180964 A1 * | 8/2007 | McCormick ............. | G01N 1/06 83/13 |

* cited by examiner

*Primary Examiner* — Jyoti Nagpaul
(74) *Attorney, Agent, or Firm* — AlphaPatent Associates, Ltd; Ricki L. Simon; Daniel J. Swirsky

(57) ABSTRACT

A biopsy sample storage device is configured to provide tissue samples that can be cut into at least two sections for different types of analysis. A first portion of the sample may be frozen for cryo-preservation, while a second portion of the same sample may be chemically preserved for histological analysis.

20 Claims, 9 Drawing Sheets

MULTI-MODAL BIOPSY STORAGE DEVICE AND METHODS

CROSS-REFERENCE TO RELATED APPLICATIONS

The present application claims the benefit of U.S. Provisional Patent Application No. 62/123,388, filed Nov. 17, 2014.

FIELD OF THE INVENTION

The present invention relates to a biopsy storage system and method which enables two or more modes of storage, preservation and analysis of a biopsy tissue sample.

BACKGROUND OF THE INVENTION

Tissue samples, for example samples obtained by biopsies, are typically preserved by deep freezing or by chemical preservation. Deep freezing, for example by liquid nitrogen, maintains the native biomolecular profile of the living tissue, but the formation of ice pellets during the freezing process damages delicate structures in the cells. Thus frozen samples are the preferred mode of preservation when the tissue is kept for future biochemical analysis. Unfortunately, the damage to intracellular structures prevents high quality microscopic analysis of the tissue, for example histo-pathology analysis and immunohistochemical (IHC) analysis. Chemical preservation is typically done by formalin, which cross-links primary amino groups in proteins and thus stabilizes the structure of the tissue. This process kills the cells and degrades many of the biomarkers that are used clinically, including proteins, peptides, DNA, and most notably RNA and its derivatives. Following tissue fixation by formalin the tissue is embedded in paraffin, which enables cutting thin sections (few micron thickness) for high quality microscopy. This process, termed FFPE—formalin-fixed paraffin-embedded—is the most common preservation method of tissue samples for pathology analysis.

Pathologists would like to obtain both the high quality histology that is provided by FFPE and the high quality substrate for biomarker analysis that is provided by frozen sections. However, taking many samples and storing some by cryopreservation and some by FFPE is not the ideal solution since the pathologist is interested in the histology information and the biomarker information from the same location in the tumor. The inhomogeneity of tumors is a well known phenomena, where different properties can be found at different sites in the same tumor. Furthermore, other modes of preservation may be needed—for example preservation that keeps viable cells for future use in cell cultures.

Thus there is a need for a system and a method that will provide the advantages of cryopreservation and of chemo preservation from the same tissue sample, and which would also have the flexibility to apply additional modes of preservation—for example to keep viable cells in the tissue.

SUMMARY OF THE INVENTION

There is provided, in accordance with embodiments of the present invention, a biopsy sample storage device. The device includes a first collection compartment having at least one cell for collection of a sample, a second collection compartment positionable adjacent to the first collection compartment and configured to hold a portion of the sample positioned within the cell of the first collection compartment, and a cutting mechanism for cutting the collected sample into a first sample portion positioned within the first collection compartment and a second sample portion positioned within the second collection compartment.

In accordance with further features in embodiments of the present invention, the device may further include a cooling device adjacent to the first collection compartment for freezing the first sample portion. The cooling device is configured to freeze the first sample portion to a temperature of, for example, less than zero degrees Celsius. The cooling device may include, for example, a thermoelectric device such as a Peltier thermoelectric device, a vapor compression cycle, a Stirling refrigeration cycle or a Joule Thomson cooler or any other system which can cool a portion of the sample.

In accordance with further features in embodiments of the present invention, the first collection compartment may be, for example, a tray. The cell in the tray has a depth which is less than a diameter of a biopsy needle such that a portion of a sample placed within the cell protrudes therefrom into the second collection compartment. The second collection compartment may be, for example, a tissue cassette, and may include openings for introduction of a stabilizing gel.

In accordance with further features in embodiments of the present invention, the cutting mechanism may be a cutting plate with a blade for insertion between the first collection compartment and the second collection compartment. The cutting plate may be insertable via linear or rotational sliding, for example. In some embodiments, a temperature probe is inserted into the second collection compartment. A control module may be connected to the temperature probe for controlling a temperature of a sample within the device.

There is provided, in accordance with additional embodiments of the present invention, a system for cryo-preservation and chemo-preservation of a single biopsy sample. The system includes a first collection compartment for holding a first portion of the single biopsy sample, a second collection compartment adjacent to the first collection compartment for holding a second portion of the single biopsy sample, a cooling device adjacent to the first collection compartment for providing a cooling effect to the first collection compartment such that the first portion of the single biopsy sample may be maintained at a frozen temperature while the second portion of the single biopsy sample is maintained at a temperature above freezing, and a cutting mechanism for separating the first portion of the single biopsy sample from the second portion of the single biopsy sample.

In accordance with further features in embodiments of the present invention, the cooling device may be a portion of a cooling apparatus, which may include a temperature probe inserted into the second collection compartment, a power supply for providing electric current to the cooling device, and a control module for controlling the amount of electric current provided from the power supply to the cooling device based on feedback from the temperature probe. The cooling device may be, for example, a thermoelectric device such as a Peltier thermoelectric device, a vapor compression cycle, a Stirling refrigeration cycle or a Joule-Thomson cooler or any other system which can cool a portion of the sample.

In accordance with further features in embodiments of the present invention, the cutting mechanism may be a cutting plate with a blade for insertion between the first collection compartment and the second collection compartment, and may be insertable via linear or rotational sliding. In some embodiments, the first collection compartment is a tray, and the second collection compartment is a tissue cassette.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which.

Figure 1A:
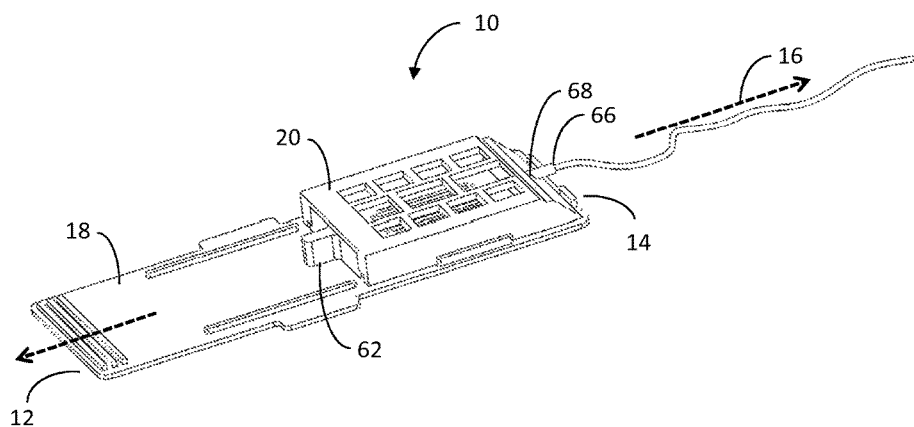
FIGS. 1A-1B are perspective illustrations of a biopsy sample storage device in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

Embodiments of the present invention are directed to systems and methods for biopsy and preservation of a tissue sample, and more particularly to a biopsy sample storage device. The device and method of the present invention are designed to provide samples which can be used for both microscopic histopathology analysis and biomarker analysis. The principles and operation of systems and methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

A device in accordance with embodiments of the present invention is a biopsy sample storage device that can store a single sample, or multiple samples, for both cryo-preservation and chemo-preservation in each sample.

The present invention aims to stabilize tissue biomarkers based on rapid, deep freezing of the tissue, and to maintain histological structures for microscopic analysis in the same biopsy sample.

In a biopsy procedure, the physician (eg, radiologist, surgeon) harvests biopsy samples using standard biopsy needles such as, for example, Quick-Core® Biopsy Needle (Cook Medical, Bloomington Ind., USA). Typically, several biopsy samples are obtained using the same needle and are placed on a tray. The samples are then generally either inserted into a vial with formalin for chemo-preservation of the sample tissue, or are cooled or frozen via various methods for cryo-preservation. It is generally not possible to perform both preservation methods on the same sample, since the two methods of preservation are mutually exclusive, wherein one method would destroy the components necessary for the other method. The present invention is directed to a device and method which allows for both cryo-preservation and chemo-preservation in the same sample.

Figure 1B:
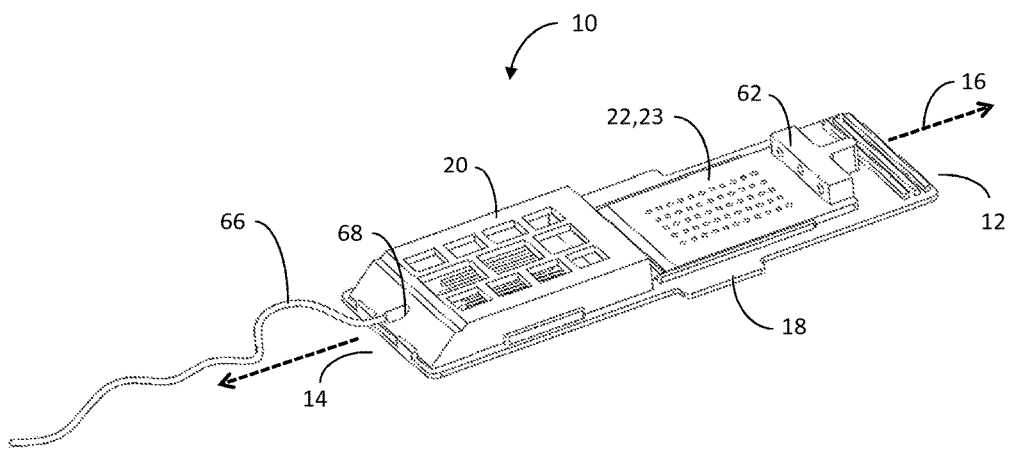

Reference is now made to FIGS. 1A and 1B, which are perspective illustrations of a biopsy sample storage device 10 in accordance with embodiments of the present invention. Device 10 has a device first end 12 and a device second end 14 opposite device first end 12 along a longitudinal axis 16. Device 10 includes a first collection compartment 18 and a second collection compartment 20. In embodiments of the invention, first collection compartment 18 is a tray for holding biopsy samples, and second collection compartment 20 is a hollow chamber configured to be positioned over at least a portion of first collection compartment 18, such that a sample placed within the hollow chamber will be partially positioned within first collection compartment 18 and partially positioned within second collection compartment 20, as will be described in greater detail hereinbelow. Device 10 further includes a cutting mechanism 23 for cutting a sample positioned within device 10 into two portions: one portion which remains within first collection compartment 18 and another portion which remains within second collection compartment 20. Cutting mechanism 23 may be, for example, a cutting plate 22, and may be designed to slide from first end 12 to second end 14 along longitudinal axis 16 to a position which is in between first and second collection compartments 18 and 20, thereby cutting the sample positioned therein along longitudinal axis 16. In other embodiments, cutting mechanism 23 may be a laser or other means of cutting a sample. Cutting plate 22 is shown in FIG. 1A in a first configuration, prior to sliding between first and second collection compartments 18 and 20, and is shown in FIG. 1B in a second configuration, in position between first and second collection compartments 18 and 20 (not visible). A temperature probe 66 may further be inserted through a side opening 68 in second collection compartment 20.

Figure 2:
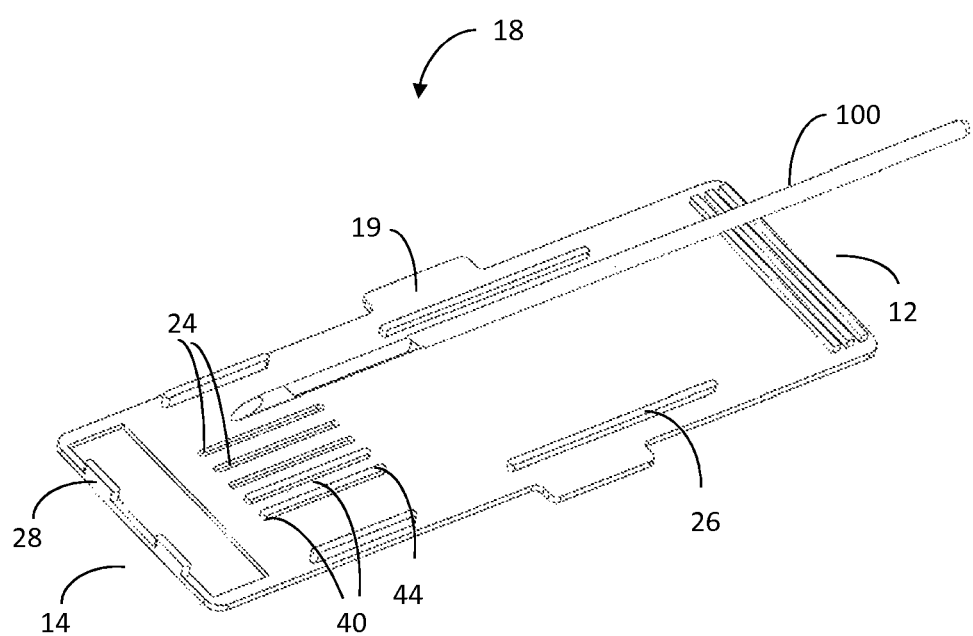
FIG. 2 is a perspective illustration of a first collection compartment of the device of FIGS. 1A and 1B.

Reference is now made to FIG. 2, which is a perspective illustration of first collection compartment 18, in accordance with embodiments of the present invention. First collection compartment 18 may be a tray 19 for receiving biopsy samples, and includes one or multiple cells 24 for receiving biopsy samples therein. Any suitable number of cells 24 may be included on first collection compartment 18. Cells 24 are shaped to only partially accommodate the biopsy samples, such that a biopsy sample placed in a cell 24 will partially protrude outwardly therefrom. For example, cell 24 may have a half-cylinder shape, and when a cylindrically shaped biopsy sample 40 taken using a biopsy needle 100 is placed within the cell 24, a bottom portion (not shown) of the sample sits within cell 24 and a top portion 44 of the sample protrudes upwardly from cell 24. The protruding portion of the sample will be enclosed within second collection compartment 20, as will be explained further hereinbelow. It should be readily apparent that tray 19 may be configured similar to, for example, a commercially available biopsy tray such as Cellsafe™ Biopsy Capsules by Ted Pella, Inc. (Redding, Calif., USA). Tray 19 is adapted to fit biopsy needle 100, and may further include tracks 26 for advancement of second collection compartment 20 and/or cutting plate 22. Tray 19 may further include a stopper 28 at second end 14 for stopping advancement of second collection compartment 20.

Figure 3:
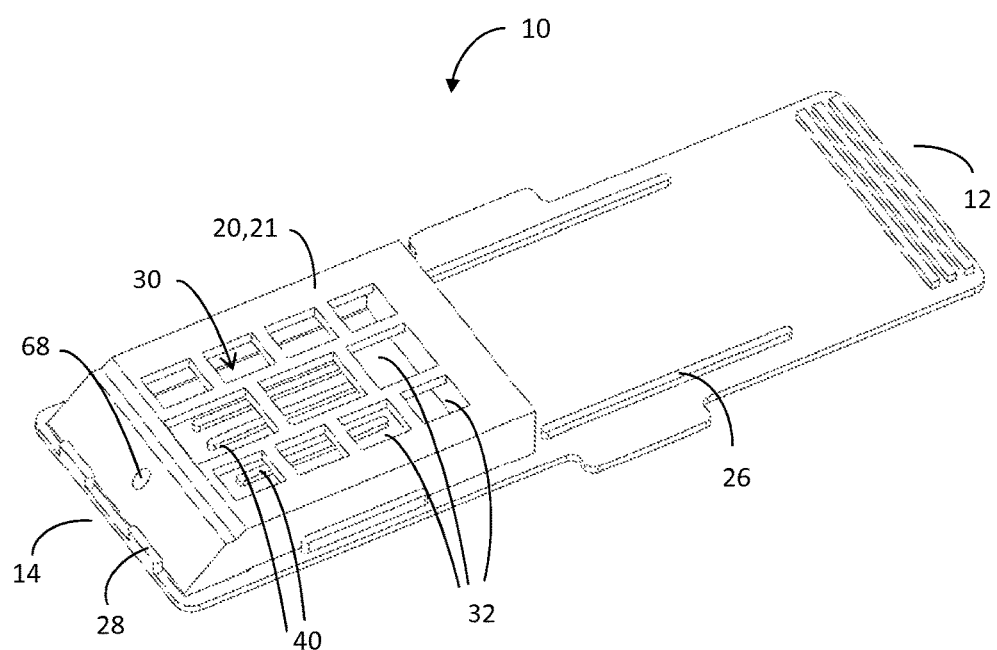
FIG. 3 is a perspective illustration showing a first and second collection compartment of the device of FIGS. 1A-1B, in accordance with embodiments of the present invention.

Reference is now made to FIG. 3, which is a perspective illustration of device 10 depicting first collection compartment 18 and second collection compartment 20 positioned adjacent to first collection compartment 18. In the embodiment shown herein, second collection compartment 20 is positioned on top of first collection compartment 18 but it should be readily apparent that other configurations are possible as well, for example, wherein first and second collection compartments 18 and 20 are configured side by side. Second collection compartment 20 may be a cassette 21 similar to tissue cassettes that are used to hold tissue specimens for pathology analysis, for example Histosette I® Tissue Cassettes by Ted Pella, Inc. (Redding, Calif., USA). Second collection compartment 20 has a hollow interior 30 and multiple openings 32 for introduction of a hardening substance therein. The hardening substance may be, for example, a gel such as HistoGel™ (Thermo Fischer Scientific, Inc., Waltham, Mass., USA), or other types of gelatin or similar substances which can be used to form a supporting block 60 (shown in FIG. 7) for biopsy samples 40. This type of gel can solidify inside cassette 21 when it is cooled by a cooling apparatus described further hereinbelow. Alternatively the substance may harden without cooling for example by using chemical solidification similar to epoxy glue. The gel may have temperature dependent rigidity, and may include for example, optimal cutting temperature (OCT) substance, polyethylene glycol, or polyvinyl alcohol.

The portions of sample 40 which are embedded within the supporting block 60 formed from the hardened substance in the cassette can then be cut and analyzed histologically, as will be described. The supporting block 60 may further act as a heat sink to prevent freezing of the portion of the sample 40 enclosed therein. A side opening 68 is shown in cassette 21 for insertion of a temperature probe, which is configured to continuously monitor a temperature of samples 40 to ensure that a top portion 44 of sample 40 is maintained at a higher temperature while a bottom portion 42 of sample 40 is at a frozen temperature.

Figure 4:
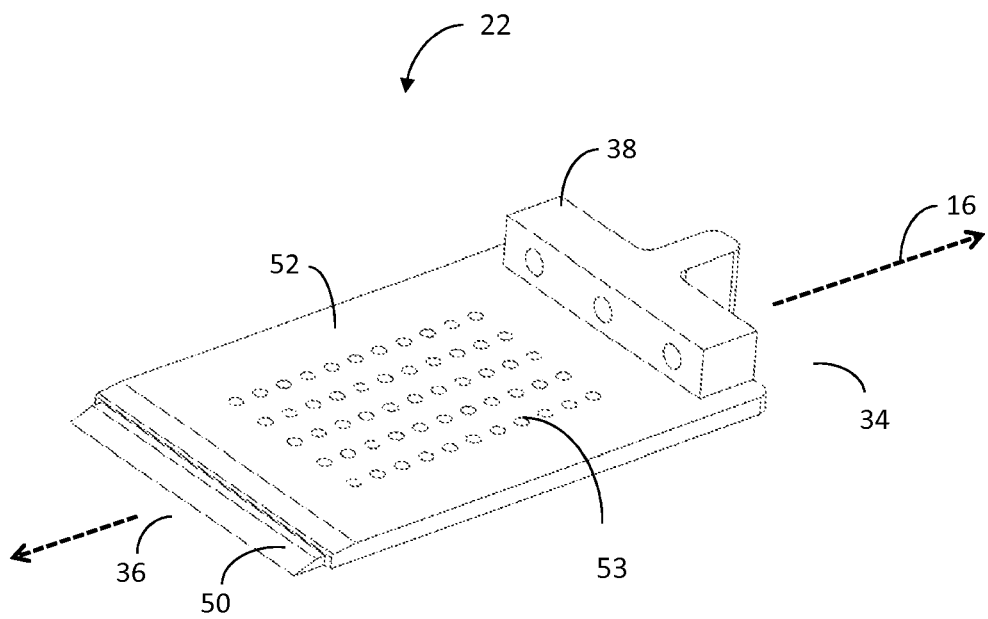
FIG. 4 is a perspective view of a cutting plate of the device of FIGS. 1A-1B, in accordance with embodiments of the present invention.

Reference is now made to FIG. 4, which is a perspective illustration of cutting plate 22, in accordance with embodiments of the present invention. Cutting plate 22 has a first end 34 and a second end 36 opposite first end 34 along longitudinal axis 16. A handle 38 at first end 34 allows for a user to grip cutting blade 22 and slide it along longitudinal axis 16. Alternatively, cutting plate may be moved via a driver mechanism. A cutting blade 50 is positioned at second end 36 for cutting sample 40 when cutting plate 22 is pushed from first end 12 to second end 14. A substantially flat plate 52 connects cutting blade 22 to handle 38. Openings 53 are included on cutting plate 22 so that formalin or another substance suitable for fixation can later be introduced into supporting block 60.

By having a portion of sample 40 positioned within first collection compartment 18 and a different portion of the same sample 40 positioned within second collection compartment 20, it is possible to store the portions of sample 40 separately using different modes. However, in order to accomplish this, the sample 40 must be sliced into two portions. It should be apparent that additional sections of sample 40 may also be cut for additional analysis modes as well.

Figure 5:
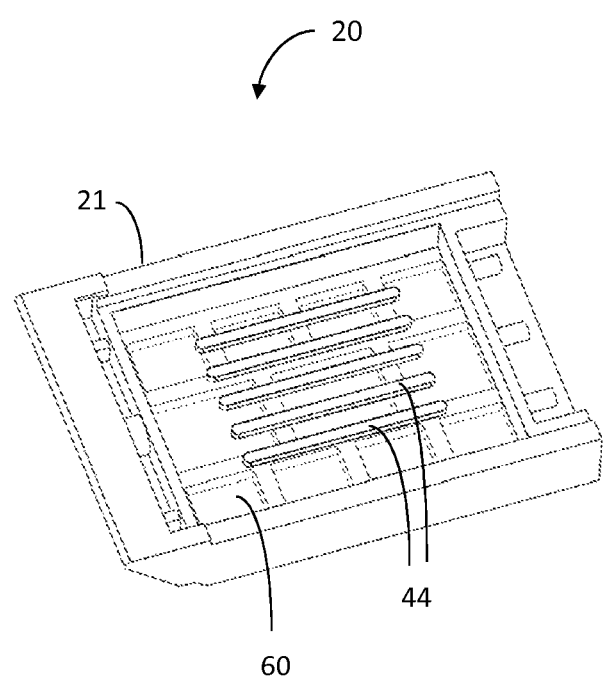
FIG. 5 is a bottom view perspective illustration of the second collection compartment of the device of FIGS. 1A-1B, shown with a sample suspended within a supporting block inside the second collection compartment, in accordance with embodiments of the present invention.

Reference is now made to FIG. 5, which is an illustration of cassette 21 with a supporting block 60 formed from introduction of a gel through openings 32 into hollow interior 30 of cassette 21. Cassette 21 is shown from a bottom view, after cutting plate 22 has cut through samples 40, with top portions 44 of samples 40 suspended inside supporting block 60. The cassette 21 with top portions 44 of samples 40 can be processed for histological analysis following the standard methodology of tissue samples processing—fixation by formalin followed by embedding in paraffin. The shape of cassette 21 is similar to the shape of standard tissue processing cassettes such as Histosette I® Tissue Cassettes mentioned above, to enable the use of standard processing apparatus like HistoCore Arcadia Tissue Embedding System by Leica Biosystems, Inc. (Buffalo Grove, Ill.).

Figure 6:
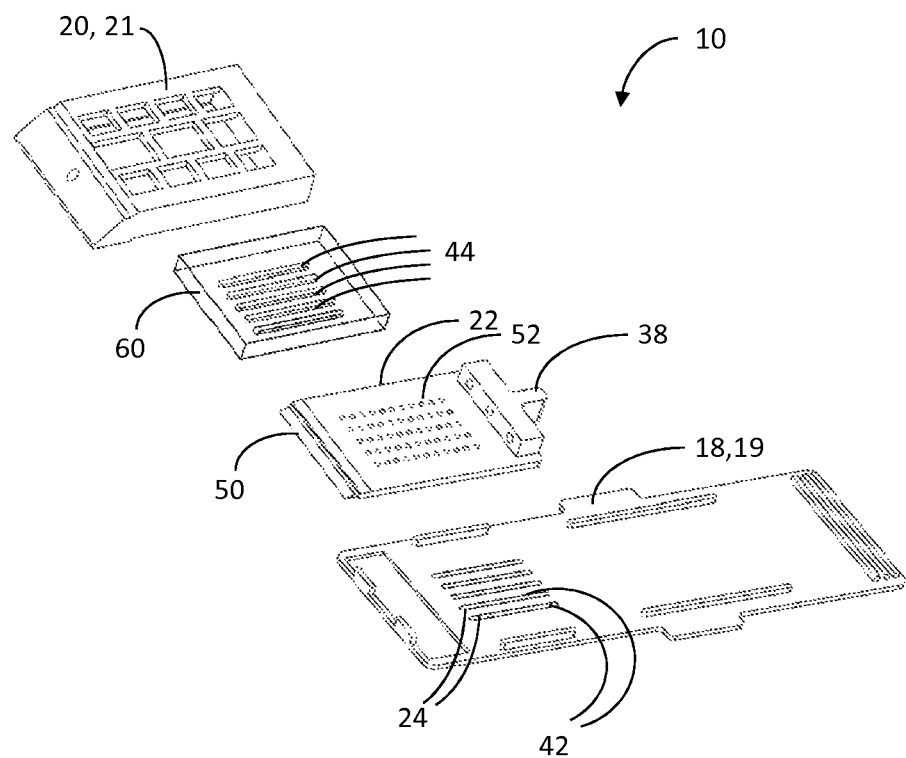
FIG. 6 is an exploded view of components of the device of FIGS. 1A-1B, in accordance with embodiments of the present invention.

Reference is now made to FIG. 6, which is an exploded view of device 10 in accordance with embodiments of the present invention. First collection compartment 18 is shown in a tray 19 configuration, as explained above. Cutting mechanism 23, shown as cutting plate 22 is positionable above first collection compartment 18. Second collection compartment 20, shown as a cassette 21, is positioned above first collection compartment 18, with cutting plate 22 in between. Supporting block 60, formed from hardening of a gel within cassette 21, is shown with top portions 44 of samples 40 suspended therein. Bottom portions 42 of samples 40 are positioned within cells 24 of tray 19. Bottom portions 42 are frozen for biomarker analysis via a cooling system, as will be described with reference to FIG. 7.

Figure 7:
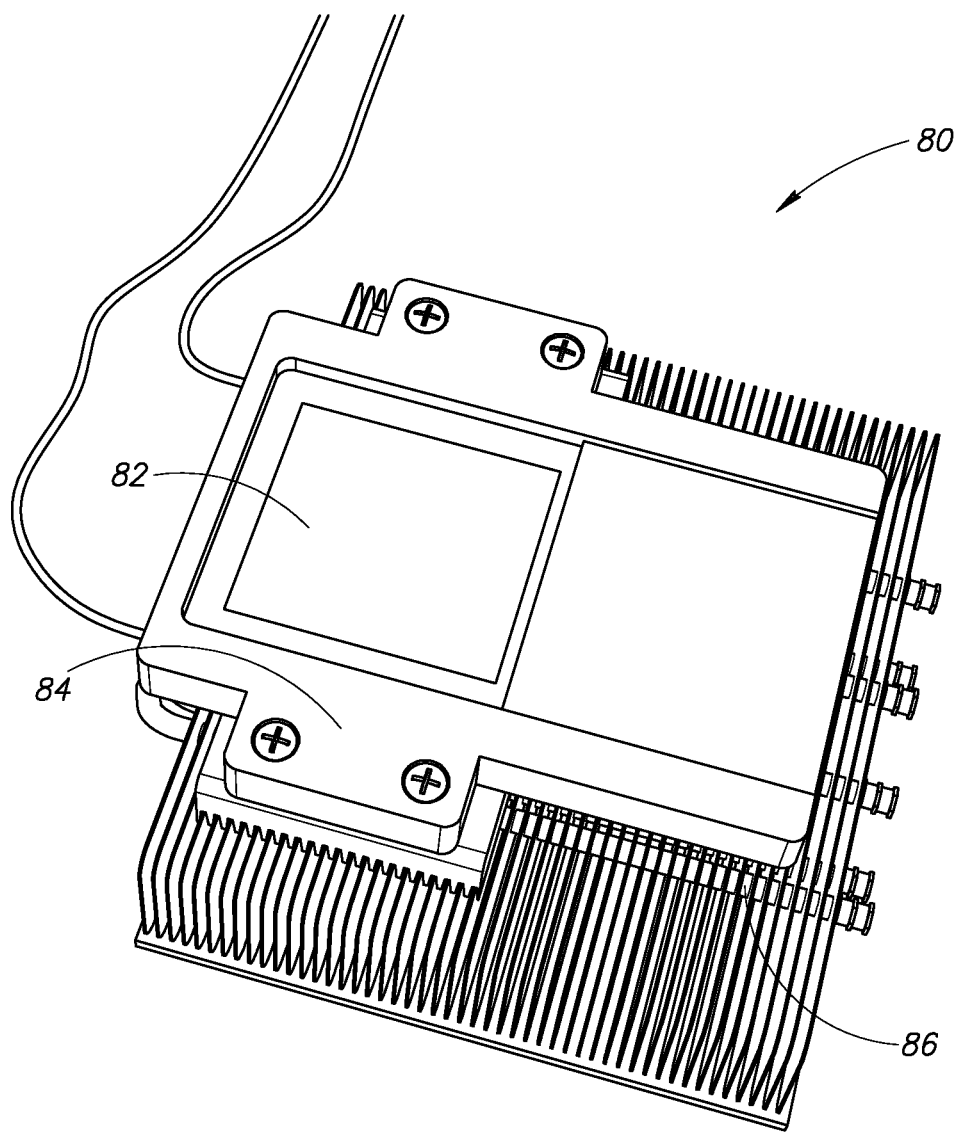
FIG. 7 is a schematic illustration of a cooling component to be used in conjunction with the device of FIGS. 1A-1B, in accordance with embodiments of the present invention.

Reference is now made to FIG. 7, which is an illustration of a cooling apparatus 80, in accordance with embodiments of the present invention. Cooling apparatus 80 may include, for example, a cooling device such as a thermoelectric chip 82, (e.g. Peltier thermoelectric cooler module by TE Technology, Inc., Traverse City, Mich.). When electrical current flows through a cooling device such as a Peltier device, one side of the device becomes cold and the other side becomes hot. The cold side is positioned to provide a cooling effect to bottom portion 42 of tissue samples 40, positioned within cells 24. In order to accomplish this, an adapter 84 may be used. Adapter 84 includes a body with thermoelectric chip 82 embedded within the body. An upper portion of adapter 84 is configured to hold first collection compartment 18 therein such that bottom portion 42 of samples 40 are positioned directly above thermoelectric chip 82. Optionally, a heat conducting paste (e.g. Arctic Silver 5 by Arctic Silver, Inc.) can be applied on top of thermoelectric chip 82 to ensure better heat transfer between first collection compartment 18 and thermoelectric chip 82, thus enhancing or speeding up the cooling effect. In addition, heat from the hot side of thermoelectric chip 82 may be removed with a heat dissipation module 86 having a heat sink attached thereto, and further including a fan that forces air through the fins of the heat sink. Such heat dissipation modules are commonly used to cool processors in computers, for example 212 EVO-CPU Cooler by Cooler Master Technology Inc. Other cooling systems that are based on other cooling methodologies (e.g. vapor-compression cycle, vapor absorption cycle, backwards Stirling cycle, Gifford-McMahon cooler, Joule-Thomson cooler) can be used to cool the samples to the required freezing temperature.

Figure 8:
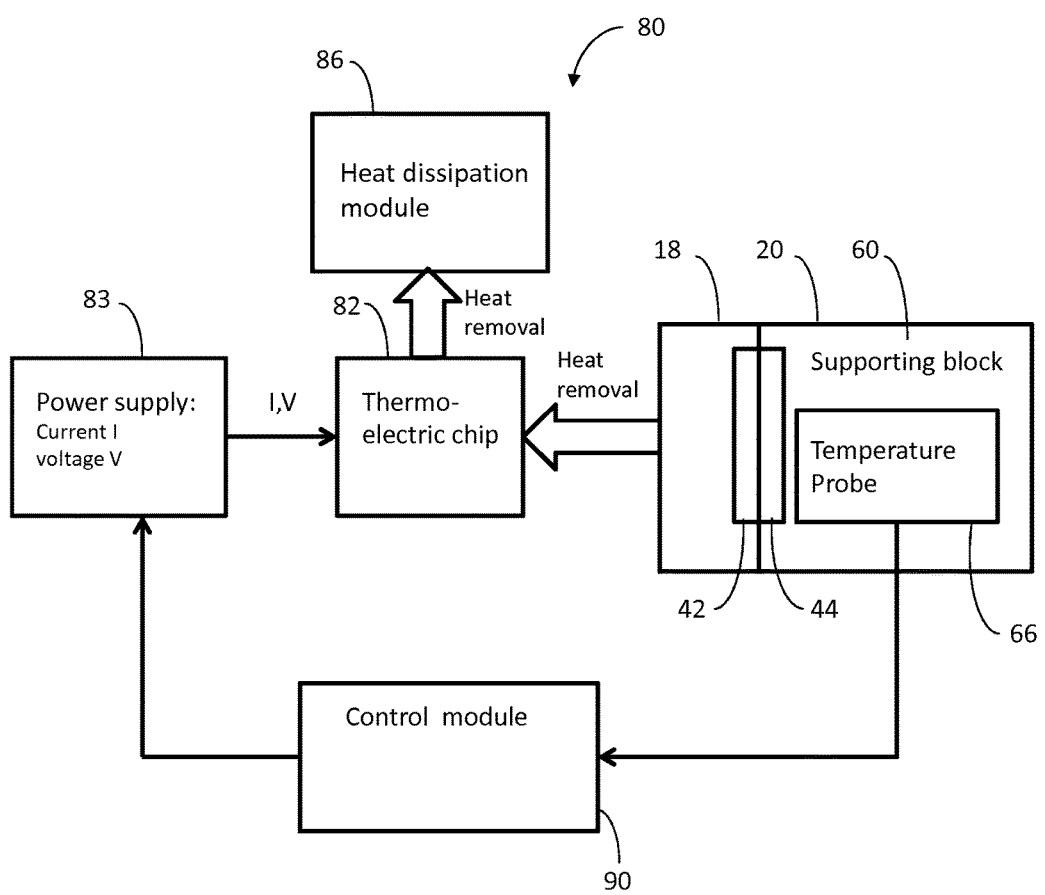
FIG. 8 is a block diagram of a control unit in communication with the device of FIGS. 1A and 1B, for controlling the temperature of portions of a sample held therein, in accordance with embodiments of the present invention.

Reference is now made to FIG. 8, which is a block diagram illustration showing the cooling apparatus 80 of device 10, in accordance with embodiments of the present invention. Although the block diagram illustration shows a thermoelectric chip 82, other cooling devices may be used as well. The temperature of supporting block 60 (i.e., the portion 44 of the sample within second collection compartment 20) is continuously measured by a control module 90 of the cooling system 80 via temperature probe 66. The control module 90 controls the operation of the cooling system to maintain the temperature of the supporting block 60 at a predefined level above the freezing point, typically at a temperature around 5 degrees Celsius, for example, although any temperature above freezing may be used. This can be done by changing the voltage supplied to thermoelectric chip 82 via a power supply 83. This ensures that the tissue portion 44 that remains in the supporting block does not freeze during the cutting process of the tissue samples by the cutting plate. At the same time, cryogenic effect (i.e. freezing) is provided to first collection compartment 18 to freeze the sample portion 42 positioned therein. Heat dissipation module 86 removes the excessive heat that is generated on the hot side of the thermoelectric chip 82.

Figure 9:
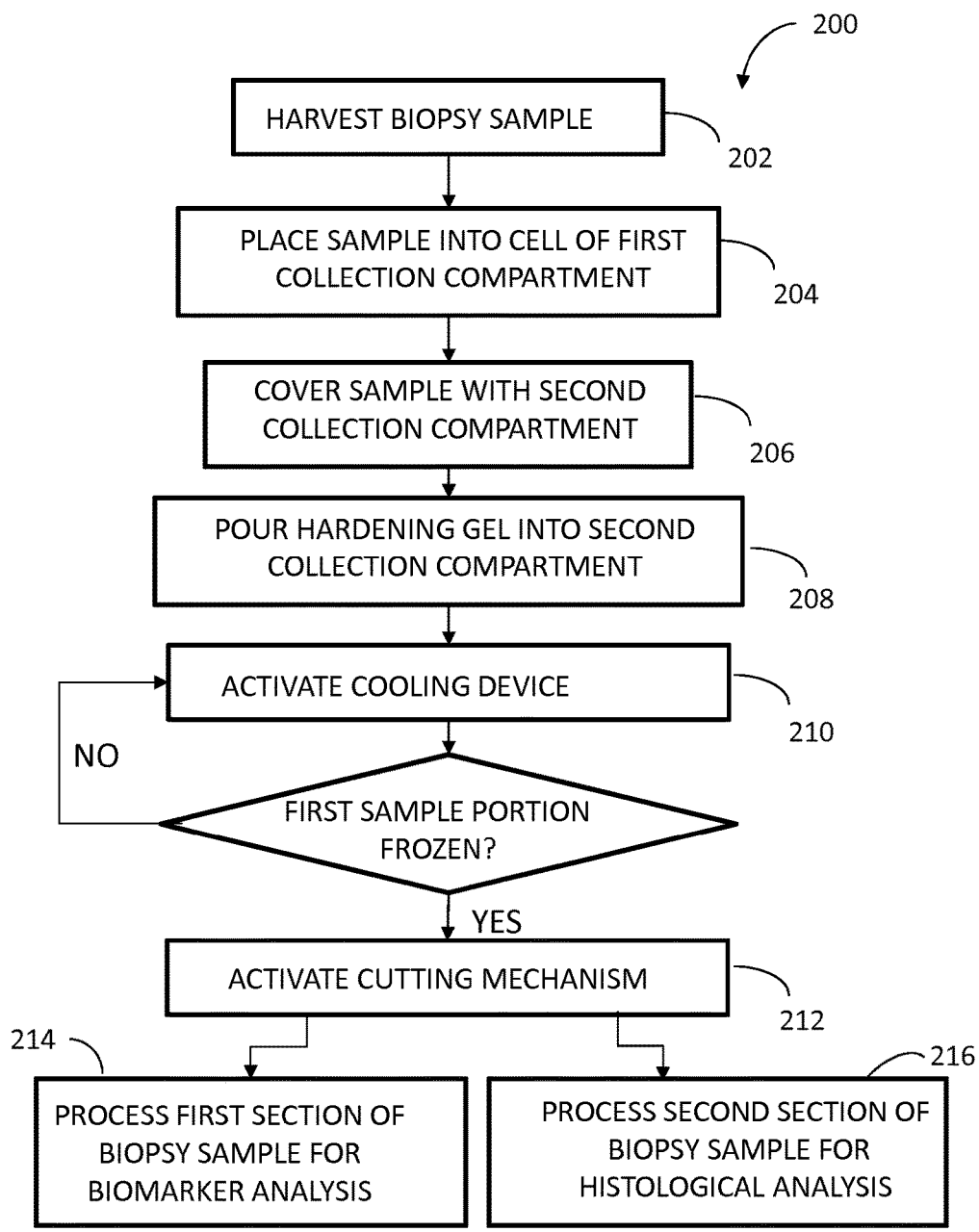
FIG. 9 is a flow chart diagrammatic illustration of a method of using the device of FIGS. 1A and 1B, in accordance with embodiments of the present invention.

Reference is now made to FIG. 9, which is a flow chart illustration of a method 200 of performing cryo-preservation and chemo-preservation on the same biopsy sample, in accordance with embodiments of the present invention. First, a physician (ie, radiologist or surgeon) harvests (step 202) a biopsy sample using a biopsy needle. In some embodiments, several biopsy samples are taken together, and placed (step 204) into suitable cells 24 located in first collection compartment 18, which may be, for example, biopsy tray 19. Cells 24 are sized such that the collected samples are configured to partially protrude therefrom. Next, a user (which may be the physician or a technician, for example), covers (step 206) the sample with second collection compartment 20, such as a cassette 21. Cassette 21 may include cutting plate 22 attached thereto. Cassette 21 with cutting plate 22 may be placed over first collection compartment 18 to fully cover the samples. Next, the user pours (step 208) a hardening gel (for example, Histogel™) into openings 32 within second collection compartment 20. Next, the user activates (step 210) the cooling device to freeze the bottom portions 42 of samples 40. Once the gel is hardened, the user activates (step 212) the cutting mechanism, for example, by pushing a cutting plate in between first collection compartment 18 and second collection compartment 20 to cut sample 40 into two sections: a bottom section 42 in first collection compartment 18 and a top section 44 in second collection compartment 20. Bottom sections are kept in a frozen state until they are processed (step 214) for biomarker analysis, and top sections 44 are processed (step 216) for histological analysis. This processing may include, for example, placing the top sections 44 of samples 40 into formalin to fix and stabilize the microscopic structure, followed by embedding in paraffin and sectioning for histopathology as is known in the art. Thus, the same sample 40 has undergone both biomarker analysis and histological analysis, while being preserved in the appropriate manner for each analysis. The spatial relation between the sample portions 44 that are used for histology analysis and the sample portions 42 that are kept frozen is maintained. This enables the pathologist to microdissect the tumor region in the frozen sections according to the tumor region as determined by histology analysis of the corresponding histology sections prepared from sample portions 44.

In some embodiments, top sections 44 may be processed for other needs, for example, added to a tissue culture media for growing tumor cells.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

What is claimed is:

1. A biopsy sample storage device, the device comprising:
    a first collection compartment, said first collection compartment comprising a tray having at least one cell for collection of a sample, wherein the cell is sized to enclose only a portion of a single sample, wherein when a first sample portion of the single sample is in the cell, a second sample portion of the single sample is protruding out from the cell;
    a second collection compartment positionable adjacent to said first collection compartment wherein the second collection compartment is a hollow chamber having a biochemical preservation substance therein, said second collection compartment configured to hold the second sample portion which is protruding out from the cell while the first sample portion is simultaneously also positioned within the cell of the first collection compartment; and
    a cutting mechanism for separating the first sample portion positioned within the first collection compartment from the second sample portion positioned within the second collection compartment.

2. The biopsy sample storage device of claim 1, further comprising a cooling device adjacent to said first collection compartment for freezing the first sample portion.

3. The biopsy sample storage device of claim 2, wherein the cooling device is configured to freeze the first sample portion to a temperature of less than zero degrees Celsius.

4. The biopsy sample storage device of claim 2, wherein the cooling device comprises at least one of: a thermoelectric device, a vapor compression cycle, a Stirling refrigeration cycle or a Joule-Thomson cooler.

5. The biopsy sample storage device of claim 1, wherein the at least one cell has a depth which is less than a diameter of a biopsy needle.

6. The biopsy sample storage device of claim 1, wherein said second collection compartment is a tissue cassette.

7. The biopsy sample storage device of claim 1, wherein the second collection compartment comprises openings for introduction of the biochemical preservation substance.

8. The biopsy sample storage device of claim 1, wherein the cutting mechanism is a cutting plate with a blade, wherein said cutting plate and blade are configured for insertion between the first collection compartment and the second collection compartment such that in a first configuration, said cutting mechanism is positioned outside of said first and second collection compartment and in a second configuration, said cutting mechanism is positioned between said first and second collection compartments.

9. The biopsy sample storage device of claim 8, wherein movement from said first configuration to said second configuration is done via linear or rotational sliding.

10. The biopsy sample storage device of claim 1, further comprising a temperature probe inserted into the second collection compartment.

11. The biopsy sample storage device of claim 10, further comprising a control module connected to the temperature probe for controlling a temperature of the sample within the device such that the first sample portion is maintained at a first temperature while the second sample portion is maintained at a second temperature which is different than said first temperature.

12. The biopsy sample storage device of claim 11, wherein said first temperature is below freezing and said second temperature is above freezing.

13. The biopsy sample storage device of claim 1, wherein said biochemical preservation substance is a formalin fixation substance.

14. A system for cryo-preservation and chemo-preservation of a single biopsy sample, the system comprising:
   a first collection compartment having a cell sized for holding only a first portion of the single biopsy sample, and wherein a second portion of the single biopsy sample protrudes out from said first collection compartment while said first portion is held within said first collection compartment;
   a second collection compartment adjacent to the first collection compartment for holding the second portion of the single biopsy sample while said first portion of the single biopsy sample is in said first collection compartment, such that said first portion is preserved in the first collection compartment and said second portion is preserved in the second collection compartment, said second collection compartment having a biochemical preservation substance therein;
   a cooling device adjacent to the first collection compartment, the cooling device for providing a cooling effect to the first collection compartment, said cooling device configured such that the first portion of the single biopsy sample is maintained at a frozen temperature while the second portion of the single biopsy sample is maintained at a temperature above freezing; and
   a cutting mechanism for separating the first portion of the single biopsy sample from the second portion of the single biopsy sample.

15. The system of claim 14, wherein the cooling device is a portion of a cooling apparatus, the cooling apparatus further comprising:
   a temperature probe inserted into the second collection compartment;
   a power supply for providing electric current to the cooling device; and
   a control module for controlling the amount of electric power provided from the power supply to the cooling device based on feedback from the temperature probe.

16. The system of claim 15, wherein the cooling device is at least one of: a thermoelectric device, a vapor compression cycle, a Stirling refrigeration cycle or a Joule-Thomson cooler.

17. The system of claim 14, wherein the cutting mechanism is a cutting plate with a blade, wherein said cutting plate and blade are configured for insertion between the first collection compartment and the second collection compartment such that in a first configuration, said cutting mechanism is positioned outside of said first and second collection compartment and in a second configuration, said cutting mechanism is positioned between said first and second collection compartments.

18. The system of claim 17, wherein movement from said first configuration to said second configuration is done via linear or rotational sliding.

19. The system of claim 14, wherein the first collection compartment is a tray.

20. The system of claim 14, wherein the second collection compartment is a tissue cassette.

* * * * *